US006930167B2

(12) United States Patent
Estes et al.

(10) Patent No.: US 6,930,167 B2
(45) Date of Patent: Aug. 16, 2005

(54) DNA ENCODING BOVINE IMMUNOGLOBULIN A INDUCING PROTEIN AND USES THEREFOR

(75) Inventors: D. Mark Estes, Rocheport, MO (US); Amy Austin, Phoenix, AZ (US); Karen Haas, Chapel Hill, NC (US)

(73) Assignee: The Curators of the University of Missouri, Columbia, MO (US)

( * ) Notice: Subject to any disclaimer, the term of this patent is extended or adjusted under 35 U.S.C. 154(b) by 103 days.

(21) Appl. No.: 09/999,256

(22) Filed: Oct. 31, 2001

(65) Prior Publication Data

US 2002/0146427 A1 Oct. 10, 2002

Related U.S. Application Data

(60) Provisional application No. 60/244,467, filed on Oct. 31, 2000.

(51) Int. Cl.$^7$ .............................................. C07K 14/00
(52) U.S. Cl. .................... 530/300; 424/278.1; 530/350; 530/351; 536/23.1; 536/23.5; 536/23.51; 536/23.52
(58) Field of Search ....................... 424/278.1; 530/350, 530/351, 300; 536/23.1, 23.5, 23.51, 23.52

(56) References Cited

U.S. PATENT DOCUMENTS

5,888,799 A    3/1999   Curtiss, III .............. 435/252.3

FOREIGN PATENT DOCUMENTS

EP          471453       2/1992    ............ C07K/7/52

OTHER PUBLICATIONS

Genbank Accession# BF713462, sequence comparison sheet.*
Austin et al., Abstract from CRWAD Meeting Nov. 7–9, 1999 #141.*
*EMBL/GenBank/DDBJ Databases*, Genetic Sequence Listing, Accession No. AC011379,(Oct. 7, 1999), 42 pages.
*EMBL/GenBank/DDBJ Databases*, Genetic Sequence Listing, Accession No. AF173827,(Sep. 29, 2000), 1 page.
Brandtzaeg, P., et al., "Immunobiology and immunopathology of human gut mucosa: humoral immunity and intraepithelial lymphocytes", *Gastroenterology*. 97(6), (1989), 1562–1584.

Clemons, Donna J., et al., "Evaluation of a subcutaneously implanted chamber for antibody production in rabbits.", *Laboratory Animal Science*. 42(3), (1992), 307–311.
Ehrhardt, Rolf O., et al., "Reciprocal regulation of mucosal surface IgA+ B cells by Ig receptor cross–linking and CD40 ligand.", *Journal of Immunology*. 157(4), (1996), 1397–1405.
Estes, D. M., et al., "Effects of type I/type II interferons and transforming growth factor–beta on B–cell differentiation and proliferation. Definition of costimulation and cytokine requirements for immunoglobulin synthesis and expression.", *Immunology*. 95(4), (1998), 604–611.
Jameson, Bradford A., et al., "A Rationally Designed CD4 Analogue Inhibits Experimental Allergic Encephalomyelitis", *Letters to Nature*, 368, (Apr. 21, 1994), 744–746.
Kehrl, John H., et al., "Transforming growth factor beta is an important immunomodulatory protein for human B lymphocytes.", *Journal of Immunology* 137(12), (1986), 3855–3860.
Kimmerly, et al., *Genbank (NCBI)*, assession # AC005575.
Lebman, D. A., et al., "The Role of TGF–(beta) in Growth, Differentiation, and Maturation of B Lymphocytes", *Microbes and Infection*, 1, (1999), 1297–1304.
Marra, et al., *Genbank (NCBI)*, assession # AA204132.
Westbrook, C. A., *Human Genome News*, 11, (1990), 2(4).
Zan, H. , et al., "CD40 Engagement Triggers Switching to IgA1 and IgA2 in Human B Cells through Induction of Endogenous TGF–(beta): Evidence for, TGF–(beta) But Not IL–10–Dependent Direct S(mu) >> S(alpha) and Sequential S(mu)>>S(gamma), S(gamma)>>S(alpha) DNA Recombination", *The Journal of Immunology*, 161, (Nov. 15, 1998), 5217–5225.
Austin, A., et al., "Characterization of a novel peptide, IGIP, which enhances IgA secretion by bovine B cells", *Abstract, CRWAD Meeting*, (Nov. 7–9, 1999), 141.

* cited by examiner

*Primary Examiner*—James Housel
*Assistant Examiner*—Myron G. Hill
(74) *Attorney, Agent, or Firm*—Schwegman, Lundberg, Woessner & Kluth, P.A.

(57) ABSTRACT

The invention provides an isolated and purified nucleic acid molecule encoding mammalian immunoglobulin A inducing protein (IGIP), and methods of using the IGIP nucleic acid molecule and IGIP.

27 Claims, 6 Drawing Sheets

LIBRARY SCREENING PROTOCOL

TRANSFECTION (3 DAYS) ⟶ ISOLATE PLASMIDS FROM CELLS
↓
BIOASSAY WITH TRANSFECTION SUPERNATANT (7 DAYS)
↓
ELISA
↓
SUBDIVIDE PLASMIDS FROM POOL THAT INDUCED HIGHEST AMOUNT OF IgA
↓
BEGIN NEXT ROUND OF SCREENING STARTING WITH TRANSFECTION OF PLASMIDS

FIG. 1

```
CCA ATT ATA CAG TAG AAT ATC ATT AAT TTG CAC TGG TTG GGG ACC

CCA TTA AGA ATG CTG AAT TTT GCC AAC TAA GAA GTA AGC AAA TGC

AAT TTA AAA AGT AAA TTT GAG CAT TCT GTA TTA AAT CTG TGC AGC

TAT TAT CAC ATG AAG AAG CGC AGT GTG TCG GGC TGT AAT ATA ACC
            Met K   K   R   S   V   S   G   C   N   I   T
ATA CTT GCT GTT GTG TTC TCC CAT CTC AGT GCT GGG AAC TCA CCA
 I   L   A   V   V   F   S   H   L   S   A   G   N   S   P
TGT GGA AAC CAA GCA AAT GTG TTG TGC ATC AGC CGG CTT GAG TTT
 C   G   N   Q   A   N   V   L   C   I   S   R   L   E   F
GTT CAA TAT CAA AGC TGA AAC TAG CGA GGT CTG CTG TAC TGC TTA
 V   Q   Y   Q   S  Stop
TTG AAG TAT TGT GAT TCT TTT AGG CAT TGA TTC TTA AAA AAT ATA

TAC TGT AAC AGT ATA CTT TGT ACA GAT TTA AAT TTT ATT TGA AAA

AAA TGA AAT AAA GTA GGC AAA AAA ATA AAA AAA AAA AAA AAA AAA

Nucleotide Comparison between Bovine, Human and Mouse genes

```
Bovine    1  aatatcattaatttgcactgttggggacccatt-aagaatgctgaatttt-gccaacta  59
Human  4660  aatatcattaatttgcactgtttggggacccatt-aagaatgctgaatttt-gccaacta 4719
Mouse     1  ........attaattgcactgttttgggacccatt-aagaatgctgaattttgccaacta  60

Bovine   60  agaagtaagcaaatgcaattaaaaagtaaatttgagcattctgtattaaatctgtgcag  119
Human  4720  agaagtaagcaaatgcaattaaaaagtaaatttgagcattctgtattaaatatgtgcag 4779
Mouse    61  aaagtaagcaaatgcaattaaaagtaaatttgagcattctgtgttaaatatgtgcag   120

Bovine  120  ctattatcacatgaagaagcgcagtgtgtcgggctgtaatataaccatactgctgttgt  179
Human  4780  ttattatcacatgaagaaacgcagtgtgtcgggctgtaatattaccatatttgctgtcat 4839
Mouse   121  ttattatcatatgaagaagcgcagtgtgttgggctgtaatataaccatatttgctgtcat 180

Bovine  180  gttctcccatccagtgctgggaactcaccatgtgaaaccaagcaaatgtgttgtgcat  239
Human  4840  gttcccatccagtgctgggaactcaccatgtgaaaccaagcaaacgtgttgtgcat   4899
Mouse   181  gttcccatccagtgctgggaactcaccatgtgaaaccaagcaaccgtgttgtgcat   240

Bovine  240  cagccggcttgagtttgttcaatatcaaagctgaaa-ctagcgaggtctgctgtactgct 298
Human  4900  cagccggcttgagtttgttcaatatcaaagctgaaactagcgaggtctgctgtactgct 4959
Mouse   241  cagccggcttgagtttgttcaatatcaaagctgaag-ctagcgaggtctgctgtactgct 300

Bovine  299  tattgaagtattgtgattcttttaggcattgattcttaaaaatatatactgtaacagta  358
Human  4960  tattgaagtattgtgattattttaggcattgattcttacaaaatatatactgtaacagta 5019
Mouse   301  tattgaagtattgtgattcttttaggcattgttcttacaaaatatatactgtaacagta  360

Bovine  359  tactttgtacagatttaaattttatttgnnnnnnntgaaataagtaggcaaaa       412
Human  5020  tactttgtacagatttaaattttatttgaaaaaa-tgaaataagtaggcaaaa       5072
Mouse   361  tactttgtacagatttaaatttttattg                                381
```

FIG. 3A

Amino acid Comparison between Bovine, Human, and Mouse genes

```
Bovine    Met K K R S V S G C N I T I L A V V F S H L S A G N S P C G N Q A
Human     Met K K R S V S G C N I T I F A V M F S H L S A G K S P C G N Q A
Mouse     Met K K R S V L G C N I T I F A V M F S H L S A G N S P C G N Q A Bovine    N V L C I S R L E F V Q Y Q S stop
Human     N V L C I S R L E F V Q Y Q S stop
Mouse     T V L C I S R L E F V Q Y Q S stop
```

DNA ENCODING BOVINE IMMUNOGLOBULIN A INDUCING PROTEIN AND USES THEREFOR

CROSS-REFERENCE TO RELATED APPLICATIONS

This application claims the benefit of the filing date of U.S. application Ser. No. 60/244,467, filed on Oct. 31, 2000, the disclosure of which is incorporated by reference herein.

STATEMENT OF GOVERNMENT RIGHTS

This invention was funded at least in part with a grant from the Government of the United States of America (grant 96-35204-3584 from the U.S. Department of Agriculture). The Government may have certain rights to the invention.

BACKGROUND OF THE INVENTION

Regulation of immunoglobulin A (IgA) synthesis is multifactorial, e.g., T cells, dendritic cells, and cytokines regulate isotype switching to IgA, although the exact mechanisms by which they control isotype switching are unknown. IgA is the predominant immunoglobulin isotype in mucosal secretions, tears, saliva and the upper respiratory tract and provides the first line of defense against many pathogens, functioning in agglutination and neutralization of bacteria, viruses, and toxins. IgA accounts for 70–90% of all immunoglobulins in the gut-associated lymphoid tissue (GALT) and IgA production by B cells is one of the main mechanisms of defense in the GALT (Brandtzaeg et al., 1989). The primary lymphoid organs of the GALT are the Peyer's Patches (PP) and associated areas of the small intestine, but tonsils, adenoids and appendix are also considered to be part of the GALT (Brandtzaeg et al., 1989; Delacroix et al., 1985).

Some of the cytokines and costimulators that have been identified which regulate expression of IgA include IL-10, IL-2, vasoactive intestinal peptide (VIP), and transforming growth factor beta (TGF-β). TGF-β requires a well-documented switch factor for IgA (Coffman et al., 1989; Fayette et al., 1997). Supporting evidence for the effect of TGF-β on switch differentiation is provided by TGF-β responsive elements being identified in the regulatory regions of several $C_H$ genes (Lin et al., 1992). Under certain conditions, TGF-β requires dual B cell stimulation (via CD40 and anti-IgM) to significantly enhance IgA switching (McIntyre et al., 1995). The second activation signal through the B cell receptor may make the B cells more receptive to TGF-β signaling. Alternatively, since TGF-β has dramatic negative effects on both B and T cell proliferation, the second signal might be necessary to maintain the cell or drive the cell through the cell cycle (Kehrl et al.; 1986, Kehrl et al., 1991; Moses et al., 1990).

There is much evidence suggesting that unidentified regulators of IgA exist, particularly in the environment of the GALT. First, because TGF-β is ubiquitously found in lymphoid tissues, one would predict that IgA isotype switching would also be widespread in all lymphoid tissues. However, IgA switching predominantly occurs in the PPs (Erhardt et al., 1996). Secondly, TGF-β at optimal concentrations for cell survival induces only a small fraction of sIgM⁺ B cells to undergo IgA switch differentiation. In particular, in cattle, very few regulators of IgA B cell differentiation are known. B cells stimulated via CD40 and anti-IgM in the presence of TGF-β and IL-2 have enhanced production of IgA in cattle (Estes et al., 1998). However, other known IgA regulators for mice and/or humans, including VIP, IL-5, IL-6 and IL-10, have been tested in cattle, but do not induce IgA production from B cells.

Thus, what is needed is the identification of regulator(s) of IgA⁺B cell differentiation, e.g., regulators that exist in the microenvironment of the gut.

SUMMARY OF THE INVENTION

The invention provides an isolated nucleic acid molecule (polynucleotide) comprising a nucleic acid segment that encodes an IgA-inducing protein (IGIP), or a biologically active portion thereof. Preferably, the polynucleotide is not SEQ ID NO:12. To identify soluble factors that control regulation of IgA expression, a cDNA library from activated cells derived from bovine GALT (Peyer's Patch and mesenteric lymph node cells) were inserted into a mammalian expression vector. A bioassay in which a surrogate T cell is a costimulator was employed to identify and enrich for biologically relevant cDNAs. The cDNA encoding bovine IGIP (SEQ ID NO:7 is encoded by SEQ ID NO:6) was identified in two independent screens. Bovine IGIP was synthesized and screened for activity in the bioassay system. The results indicated that the activity for the synthesized protein was consistent with that observed for the transfected cDNA and thus post translational modification is not essential for induction of IgA synthesis from IgM B cells. Bovine IGIP induced IgA secretion from B cells stimulated via CD40 alone or a combination of CD40 and BCR signaling. Importantly, IGIP is able is able to induce IgA production from B cells under stimulation conditions in which TGF-β cannot. At least three distinct pathways control the regulation of IgA expression, one of which involves the GALT-derived peptide, IGIP.

Further, bovine IGIP was expressed in a variety of different tissues, including both lymphoid and non-lymphoid tissues. Moreover, bovine IGIP has homologs in humans (SEQ ID NO:8 encoded by SEQ ID NO:11) and mice (SEQ ID NO:9 encoded by SEQ ID NO:12). Thus, IGIP regulates IgA by acting as a switch factor, requires TFB-β for induction, and is expressed in a variety of tissues.

Hence, the invention provides an isolated polynucleotide comprising a nucleic acid segment encoding IGIP, e.g., a mammalian IGIP, or a biologically active portion thereof. Preferably, the nucleic acid segment has at least about 80%, 85%, 90%, 95%, 97%, 98% and up to 99%, but less than 100%, contiguous nucleic acid sequence identity to SEQ ID NO:6, SEQ ID NO:11 or SEQ ID NO:12, e.g., as calculated following the alignment shown in FIG. 3, and encodes a gene product which has substantially the same biological activity as SEQ ID NO:5, SEQ ID NO:13 or SEQ ID NO:14. The invention also provides an isolated DNA sequence that hybridizes to the complement of any of SEQ ID NO:6, SEQ ID NO:11 or SEQ ID NO:12 under any one of the stringent conditions in sections 9.47–9.51 of Sambrook et al., *Molecular Cloning: A Laboratory Manual*, Cold Spring Harbor Laboratory, Cold Spring Harbor, N.Y. (1989), which is specifically incorporated by reference herein. For example, stringent conditions are those that (1) employ low ionic strength and high temperature washing, e.g., 0.015 M NaCl/ 0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0. 1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dedecylsulfate (SDS), and 10% dextran sulfate at 42° C., with washes at 42° C. in 0.2×SSC and 0.1% SDS.

Preferred isolated mammalian IGIP polynucleotides are polynucleotides obtained from the subclass Eutheria, e.g., from the order Carnivora, Primate, Probscidea, Insectivora, Artiodactyla, Cetacea, Chiroptera, Dermaptera, Edentata, Hyracoidean, and Perissodactyla, but not from Rodentia.

The polynucleotides of the invention may be DNA or RNA, single stranded or double stranded. Also provided are antisense IGIP sequences, vectors or expression cassettes comprising sense or antisense IGIP sequences, and host cells comprising one or more of those sequences, which cells are useful to express recombinant IGIP. Preferred host cells are eukaryotic cells, e.g., plant, yeast, insect or mammalian, for instance, human, non-human primate, feline, bovine, canine, equine, ovine, swine or caprine, cells, although prokaryotic host cells are also envisioned.

Also provided is isolated and purified mammalian IGIP, a biologically active portion, an analog or a derivative thereof. As used herein, a biologically active portion, an analog or a derivative of IGIP has substantially the same activity as IGIP having SEQ ID NO:5 (the mature form of SEQ ID NO:7), SEQ ID NO:13 (the mature form of SEQ ID NO:8) or SEQ ID NO:14 (the mature form of SEQ ID NO:9). For instance, IGIP activity includes the induction of IgA secretion from peripheral B cells stimulated with CD40L or CD40L-DAP3 cells and IL-2, CD40L and anti-IgM antibody, or CD40L, or enhances Ig production in vivo in animals, e.g., in guinea pigs or a bovine-mouse chimera. Preferably, the IGIP is bovine (e.g., SEQ ID NO:7, a biologically active portion, an analog or a derivative thereof), murine (e.g., SEQ ID NO:8, a biologically active portion, an analog or a derivative thereof) or human (e.g., SEQ ID NO:9, a biologically active portion, an analog or a derivative thereof). Also provided is an isolated antibody that specifically binds to mammalian IGIP, e.g., IGIP comprising SEQ ID NO:5, SEQ ID NO:7, SEQ ID NO:8, SEQ ID NO:9, or a biologically active portion thereof.

Mucosal adjuvant materials are highly sought after due to the desire and ease of administration to inoculate individuals via oral or respiratory routes. The problem with existing agents is over toxicity. As IGIP is a naturally occurring immune response enhancing protein, toxicity is minimized. Thus, the invention provides an immunogenic composition comprising an immunogen and an effective adjuvant amount of IGIP, a biologically active portion, an analog or a derivative thereof. Preferably, the immunogenic composition is adapted for parenteral, oral or intranasal administration to a mammal so as to induce a protective immune response. Hence, the invention further provides a method to enhance the immune response of a mammal to an immunogen, comprising: contacting a mammal with an immunogen and an amount of IGIP effective to enhance the immune response of the mammal to the immunogen. The immunogen is preferably administered at the same time and by the same route as IGIP, i.e., concurrently, however, the immunogen may be administered at a different time and/or by a different route than IGIP. Preferred amounts of IGIP, a biologically active portion, analog or derivative thereof, include 0.1 to 100 micrograms, preferably 1 to 50 micrograms, and more preferably 5 to 25 micrograms.

BRIEF DESCRIPTION OF THE FIGURES

FIG. 1. Library screening protocol. To identify IgA switch factors, pools of library plasmids from a bovine GALT cDNA expression library were transfected into BNLSV A.8 cells. The culture supernatant was collected after 72 hours, and the plasmids were isolated from the cells. Bioassays were then conducted to determine if the supernatant contained proteins that induced IgA production. In the bioassay, peripheral blood B cells were stimulated with 10% library supernatant, CD40L-DAP3 cells and IL-2 for 7 days. The bioassay supernatant was tested by ELISA for secreted bovine IgM, IgG, and IgA. The isolated plasmids from BNLSV A.8 for the pool inducing the highest IgA levels were divided into 4 subpools, transformed into E. coli, grown up in culture and the plasmids extracted. The subpool plasmids were then used in the next round of screening, following the above protocol.

FIG. 2. Nucleotide and amino acid sequence of the insert in one library clone (clone 2). The top line of each row represents the nucleotide sequence of the library clone insert (451 nucleotides) (SEQ ID NO:6) and amino acid sequence of the longest open reading frame in the insert (47 amino acids) (SEQ ID NO:7) is shown below the bold-faced nucleotides.

FIG. 3A. Nucleotide sequence alignment between bovine library clone 2, a region on human chromosome 5, and a mouse cDNA clone. The top line is bovine clone 2 (SEQ ID NO:15, the middle line is a region on human chromosome 5 (Genbank Accession # AC 005575; SEQ ID NO:11), and the bottom line is a mouse cDNA clone (Genbank Accession # AA204132; SEQ ID NO:12). The bovine clone has 96% nbcleotide sequence homology with the human sequence and 93% homology with the mouse sequence.

FIG. 3B. The predicted amino acid sequence of the open reading frame in the sequences in FIG. 3A (bovine IGIP, SEQ ID NO:7; human IGIP, SEQ ID NO:8; and murine IGIP, SEQ ID NO:9). There is 94% and 91% homology between the amino acid sequences of bovine and human, and bovine and murine, IGIP, respectively. The signal sequence has 23 amino acids.

DETAILED DESCRIPTION OF THE INVENTION

I. Definitions

Figure 4:
FIG. 4. Tissue expression of IGIP as determined by RT-PCR. RT-PCR was conducted on total RNA extracted from various bovine tissues. IGIP mRNA was present in spleen, thymus, liver, MLN and PP. Controls included RNA samples without RT and RT-PCR of RNA samples for G3PDH.

As used herein, the terms "isolated and/or purified" refer to in vitro preparation, isolation and/or purification of an IGIP DNA or protein from its natural cellular environment or from association with other components of the cell, so that it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. For example, "isolated IGIP nucleic acid" is RNA or DNA containing greater than 9, preferably 36, and more preferably 45 or more, sequential nucleotide bases that encode at least a portion of an IGIP, or a RNA or DNA complementary thereto, that is complementary or hybridizes, respectively, to RNA or DNA encoding the IGIP and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell.

An isolated nucleic acid molecule means a polymeric form of nucleotides (polynucleotides) of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant (substituted) polynucleotide. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phophoroselenoate, phosphorodiselenoate, phosphoroanilothioate, phosphoraniladate, phosphoroamidate, and the like. An oligonucleotide or polynucleotide of the invention can include a label for detection, if desired.

The term "isolated polypeptide" means a polypeptide encoded by cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of IGIP open reading frame sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments (portions) of the nucleic acid molecules of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 97%, about 98%, about 99%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff (1972) and the supplement thereto. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. For computer based algorithms, default parameters are preferably employed.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, preferably at least about 97%, and more preferably at least about 98 percent sequence identity.

As used herein, the terms "label" or "labeled" refer to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides are known in the art and may be used. Examples of labels for polypeptides include, but are not limited to, the following: radioisotopes (e.g., $^{3}H$, $^{14}C$, $^{35}S$, $^{125}O$, $^{131}I$), fluorescent labels (e.g., FITC, rhodamine, lanthanide, phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

IGIP which are subjected to chemical modifications, such as esterification, amidation, reduction, protection and the like, are referred to as IGIP "derivatives." For example, a modification known to improve the stability and bioavailability of peptides in vivo is the cyclization of the peptide, for example through one or more disulfide bonds. A preferred modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like.

Also included within the scope of the term "derivative" is linear reverse D (LRD) and cyclized forward L (CFL) derivatives. LRD derivatives have the reverse (i.e., C-terminal to N-terminal) sequence of the peptide with all D-form amino acids, but are not cyclized. CFL derivatives have the forward (i.e., N-terminal to C-terminal) sequence of the peptide with all L-form amino acids, but with additional N and C terminal cys residues (if the peptide sequence does not already have cys residues at either the N or the C terminal position), followed by oxidative cyclization, or cyclization by an alternative method. Other "derivatives" of the invention include branched peptides, circular, branched and branched circular peptides.

It is also envisioned that the IGIP, biologically active portions, analogs and derivatives thereof, of the invention may comprise moieties other than the portion which enhances the IgA immune response such as antibodies or fragments thereof or fusion proteins, nucleic acid molecules, sugars, lipids, fats, a detectable signal molecule such as a radioisotope, e.g., gamma emitters, paramagnetic molecules or sound wave emitters, small chemicals, metals, salts, synthetic polymers, e.g., polylactide and polyglycolide, surfactants and glycosaminoglycans, which preferably are covalently attached or linked to the portion of the IGIP analog or derivative thereof, so long as the other moieties do not alter the biological activity of the IGIP, biologically active portion, analog or derivative thereof. Also envisioned is an IGIP, biologically active portion, analog or derivative that is non-covalently associated with the moieties described above.

II. Nucleic Acid Molecules of the Invention

1. Sources of the Nucleic Acid Molecules of the Invention

Sources of nucleotide sequences from which the present nucleic acid molecules encoding an IGIP or the nucleic acid complement thereof, include total or polyA$^+$ RNA from any eukaryotic, preferably mammalian, cellular source from which cDNAs can be derived by methods known in the art. Other sources of the DNA molecules of the invention include genomic libraries derived from any eukaryotic cellular source. Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular IGIP.

2. Isolation of a Gene Encoding an IGIP

A nucleic acid molecule encoding an IGIP can be identified and isolated using standard methods, as described by Sambrook et al. (1989). For example, reverse-transcriptase PCR (RT-PCR) can be employed to isolate and clone IGIP cDNAs. Oligo-dT can be employed as a premier in a reverse transcriptase reaction to prepare first-strand cDNAs from isolated RNA which contains RNA sequences of interest, e.g., total RNA isolated from human tissues. RNA can be isolated by methods known to the art, e.g., using TRIZOL® reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al.(1987); Erlich (1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic IGIPs. One primer is prepared which is predicted to anneal to the antisense strand, and another primer prepared which is predicted to anneal to the sense strand, of a DNA molecule which encodes an IGIP.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode an IGIP is to screen a cDNA library. Screening for DNA fragments that encode all or a portion of a cDNA encoding an IGIP can be accomplished by probing the library with a probe which has sequences that are highly conserved between genes believed to be related to the IGIP, e.g., the homolog of a particular IGIP from a different species, or by screening of plaques for binding to antibodies that specifically recognize the IGIP. DNA fragments that bind to a probe having sequences which are related to the IGIP, or which are immunoreactive with antibodies to the IGIP, can be subcloned into a suitable vector and sequenced and/or used as probes to identify other cDNAs encoding all or a portion of the IGIP.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al.(1981), and Goeddel et al. (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Encompassed within the phrase "IGIP nucleic acid" is a nucleic acid molecule encoding amino acid sequence variants (one or more amino acid substitutions) of a particular IGIP so long as the peptide having the variant amino acid sequence has substantially the same activity as an IGIP having SEQ ID NO:5, SEQ ID NO:13 or SEQ ID NO:14. Such variants are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the IGIP peptide.

Oligonucleotide-mediated mutagenesis is a preferred method for preparing amino acid substitution variants of an IGIP. This technique is well known in the art as described by Adelman et al. (1983). Briefly, IGIP DNA is altered by hybridizing an oligonucleotide encoding the desired mutation to a DNA template, where the template is the single-stranded form of a plasmid or bacteriophage containing the unaltered or native DNA sequence of the IGIP. After hybridization, a DNA polymerase is used to synthesize an entire second complementary strand of the template that will thus incorporate the oligonucleotide primer, and will code for the selected alteration in the IGIP DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. (1987). Thus, the DNA that is to be mutated may be inserted into one of these vectors to generate single-stranded template. Production of the single-stranded template is described in Sections 4.21–4.41 of Sambrook et al. (1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the IGIP, and the other strand (the original template) encodes the native, unaltered sequence of the IGIP. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

In one embodiment of the invention, an isolated and purified DNA molecule comprising a preselected DNA segment encoding an IGIP having SEQ ID NO:7 is one where the DNA segment comprises SEQ ID NO:6, or variants of SEQ ID NO:6 having nucleotide substitutions which are "silent," which can be ascertained by reference to page D1 in Appendix D in Sambrook et al., (1989). Likewise, nucleic acid molecules encoding other mammalian IGIPs may be modified in a similar manner. Thus, nucleic acid molecules encoding at least a biologically active portion of an IGIP or the complement thereto, may be modified so as to yield nucleic acid molecules of the invention having silent nucleotide substitutions, or to yield nucleic acid molecules having nucleotide substitutions that result in amino acid substitutions.

III. Preparation of Agents Falling Within the Scope of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding an IGIP is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for an IGIP, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al., (1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding an IGIP or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the IGIP or its complement, which host cell may or may not express significant levels of autologous or "native" IGIP.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular IGIP, e.g., by immunological means (ELISAs and Western blots) or by assays described hereinabove to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides, Analogs and Derivatives Thereof

The present isolated, purified IGIP peptides, or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al. (1969); Merrifield (1963); Meienhofer (1973); Bavaay and Merrifield (1980); and Clark-Lewis et al. (1997). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given IGIP can be readily prepared. For example, amides of the IGIP of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al. (1997).

In addition, the amino acid sequence of an IGIP peptide can be modified. The modification includes the substitution of at least one amino acid residue in the peptide for another amino acid residue, including substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

One or more of the residues of the peptide can be altered, so long as the peptide is biologically active. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide can readily be determined by assaying the specific activity of the peptide variant. Assays are described in detail herein.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions peptides with non-conservative substitutions. Non-conservative substitutions entail exchanging a member of one of the classes described above for another.

Acid addition salts of the peptide or of amino residues of the peptide may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Moreover, it is also envisioned that the IGIP of the invention is modified in a manner that increases their stability in vivo, e.g., their half-life or bioavailability. These modified agents are termed "derivatives." Methods to prepare such derivatives are well known to the art. One method to stabilize peptides is to prepare derivatives which are cyclized peptides (see EPA 471,453 (amide bonds), such as that between lysine and aspartic acid side chains; EPA 467,701 (disulfide bonds); EPA 467,699 (thioether bonds). Other modifications which may increase in vivo stability are disclosed in Jameson et al. (1994); U.S. Pat. No. 4,992,463; U.S. Pat. No. 5,596,078 and U.S. Pat. No. 5,091,396.

IGIP analogs have properties analogous to those of the corresponding peptide. These analogs can be referred to as "peptide mimetics" or "peptidomimetics" (Fauchere (1986); Veber and Freidinger (1985); and Evans et al. (1987) and can be developed with the aid of computerized molecular modeling. These analogs include structures having one or more peptide linkages optionally replaced by a linkage selected from the group consisting of: —Ch$_2$NH—, —CH$_2$S—, —CH$_2$—CH$_2$—, —CH=CH-(cis and trans), —CH=CF-(trans), —COCH$_2$—, —CH(OH)CH$_2$—, and —CH$_2$SO—, by methods known in the art and further described in the following references: Spatola (1983); Spatola (1983); Morley (1980); Hudson (1979) (—CH$_2$NH—, CH$_2$CH$_2$—); Spatola (1986) (—CH$_2$—S); Hann (1982) (—CH—CH—, cis and trans); Almquist (1980) (—COCH$_2$—); Jennings-White et al. (1982) (—COCH$_2$—); EP 45665 (—CH(OH)CH$_2$—); Holladay et al (1983) (—C(OH)CH$_2$—); and Hruby (1982) 31:189–199 (—CH$_2$S —). A particularly preferred non-peptide linkage is —CH$_2$NH—. Such analogs may have greater chemical stability, enhanced pharmacological properties (half-life, absorption, potency, efficacy, etc.), altered specificity (e.g., a broad-spectrum of biological activities), reduced antigenicity, and be economically prepared. Labeling of analogs usually involves covalent attachment of one or more labels, directly or through a spacer (e.g., an amide group), to non-interfering positions(s) on the analog that are predicted by quantitative structure-activity data and/or molecular modeling. Such non-interfering positions generally are positions that do not form direct contacts with the macromolecule(s) to which the analog binds to produce the therapeutic effect. Systematic substitution of one or more amino acids of a consensus sequence with a D-amino acid of the same type (e.g., D-lysine in place of L-lysine) may also be used to generate more stable peptides.

IV. Dosages, Formulations and Routes of Administration of the Agents of the Invention The agents (e.g., IGIP, biologically active portion, analog or derivative thereof, or IGIP DNA) of the invention are administered at dosages that provide a beneficial result, e.g., an enhanced humoral or cellular immune response to an administered immunogen. The amount administered will vary depending on various factors including, but not limited to, the agent chosen, the immunogen chosen, the organism to be immunized, and if the agent or immunogen is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al. (1995); Stevenson et al. (1995); Molling (1997); Donnelly et al.(1995); Yang et al.(1996); Abdallah et al. (1995)). Pharmaceutical formulations, dosages and routes of administration for nucleic acids are generally disclosed, for example, in Felgner et al., supra.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The agent is preferably administered concurrently with the immunogen on at least one occasion.

One or more suitable unit dosage forms comprising the agents optionally comprising the immunogen of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. Preferred routes of administration, e.g., for nucleic acid based vaccines, are intramuscular, subcutaneous or intranasal. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The agents of the invention can also be formulated as elixirs or solutions for convenient oral administration or as solutions appropriate for parenteral administration, for instance by intramuscular, subcutaneous or intravenous routes.

The pharmaceutical formulations of the agents of the invention can also take the form of an aqueous or anhydrous solution or dispersion, or alternatively the form of an emulsion or suspension.

Thus, the agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable mate-rial which is impermeable to the therapeutic agent. The backing layer serves as a protective cover for the matrix layer and provides also a sup-port function. The backing can be formed so that it is essentially the same size layer as the poly-mer matrix or it can be of larger dimension so that it can extend beyond the side of the poly-mer matrix or overlay the side or sides of the poly-mer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long—term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, poly-esters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolu-tion or erosion of the matrix by skin moisture would affect the release rate of the therapeutic agents as well as the capability of the dosage unit to remain in place for convenience of re-moval.

Exemplary materials for fabricating the adhesive polymer layer include polyethylene, poly-propylene, polyurethane, ethylene/propylene copoly-mers, ethylene/ethylacrylate copolymers, ethylene/vinyl-acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane tri-methacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the agents of the invention can also be by a variety of techniques which administer the agent at or near a particular physiological location. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the agents may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other agents.

To employ the agents of the invention to enhance the immunological response of a particular immunogen, e.g., HIV or the *Haemophilis influenza* type b (Hib) capsular polysaccharide (polyribosylribitol phosphate, PRP), the agents may be conjugated to the immunogen. Thus, for example, IGIP may be covalently linked to PRP through a 6 carbon spacer molecule derived from adipic acid dihydrazide (see Gordon, Patent 83/4939, Republic of South Africa, 1984), and administered in a manner similar to that described in Eskola et al., *Lancet*, 1, 1184 (1985). However, co-administration of non-conjugated immunogen and adjuvant is also envisioned. Preferred formulations include, but are not limited to microfluidized, emulsion-oil, detergent, or ISCOM formulations. For a general description of vaccine principles and practice, see Ada, In: *Fundamental Immunology*, 2nd ed., Raven Press Ltd., N.Y., pp. 985–1030 (1989).

The invention will be further described by the following non-limiting example.

EXAMPLE

Materials and Methods
Construction of cDNA Library

Isolated lymphocytes from bovine Peyer's Patches and mesenteric lymph nodes were stimulated independently with pokeweed mitogen (10 µg/ml, Sigma, St. Louis, Mo.), concanavalin A (1 µg/ml, Sigma), phorbol myristic acetate (10 µg/ml, Sigma) and calcium ionophore (10 µg/ml Sigma) for 8 and 18 hours. A plasmid cDNA expression library was constructed from RNA isolated from pooled lymphocytes using a commercially available kit (Invitrogen, Carlsbad, Calif.). The first strand was synthesized using oligo dT with a NotI restriction site followed by a XbaI/HindIII adaptor ligation which allowed unidirectional cloning. The cDNA was cloned into a eukaryotic expression vector pcDNA3.1 (+) (Invitrogen) which has a cytomegalovirus (CMV) promoter. The library was subdivided into 16 random pools.

Transfection

COS 7 cells (American Type Culture Collection (ATCC), Bethesda, Md.) which are SV40 transformed African green monkey kidney cells, or BNL-SV A.8 cells (ATCC, Bethesda, Md.) which are SV40 transformed mouse liver cells, were plated at $1 \times 10^5$ cells in 2 ml serum-free Dulbecco's minimal essential medium (DMEM) in 6 cm dishes the day before transfection. LipofectAMINE (Gibco-BRL, Gaithersburg, Md.) was used for transfection according to the manufacturer's instructions. Briefly, plasmid DNA (2 µg) and LipofectAMINE (4 µl) were mixed in serum-free DMEM and incubated for 45 minutes at room temperature. Mock transfectants, which received only LipofectAMINE and no DNA, were used as a control. Cells were washed twice with serum-free DMEM and the DNA/LipofectAMINE mixture was added with an additional 1.6 ml serum-free DMEM. Cells were incubated for 4 hours at 37° C. in 5% $CO_2$. Then 2 ml of DMEM supplemented with 20% immunoglobulin-free horse serum was added to the cultures. After 24 hours, the medium was replaced with 2 mls DMEM supplemented with 10% immunoglobulin-free horse serum. Seventy-two hours after the start of transfection, the cell supernatant was collected. Plasmid DNA was isolated from the cells using a commercially available mini-prep kit (Qiagen, Valencia, Calif.). Plasmid DNA was transformed into *E. coli* (Top 10F', Invitrogen) using the manufacturer's instructions and cultured in Luria broth (LB) with ampicillin (50 µg/ml, Sigma). Plasmid DNA was isolated from 3 ml cultures using a commercially available mini-prep kit (Qiagen). Restriction enzyme digestion of plasmids was done with XbaI and HindIII enzymes (Promega, Madison, Wis.) according to manufacturer's instructions for 1.5 hours with 0.5 µg DNA.

Lymphocyte Purification and Culture

Peripheral blood mononuclear cells (PBMCs) were isolated from the peripheral blood of 6–12 month old Holstein or Angus heifers or steers by incubating 30 ml of red cell lysis buffer (0.15 $NH_4Cl$, 10 mM $KHCO_3$, 1 mM EDTA, $H_2O$) with 20 ml of blood for 20 minutes at room temperature. During this incubation, carbonyl iron (0.1 µg/ml) was added to the blood mixture for 20 minutes and then exposed to a magnetic field for 2 minutes to remove phagocytic cells. Following incubation, the cells were washed 3 times with Hank's buffered salt solution (HBSS). B lymphocytes were enriched by panning in the presence of 3% bovine serum albumin (BSA, Fraction V, Sigma, St. Louis, Mo.) in HBSS as described in Severson et al. (1987). Briefly, PBMCs were resuspended at a concentration of $1 \times 10^7$ cells/ml in panning solution (3% BSA, 10 mM Tris, 50 µg/ml gentamicin, 0.0025 mM $CaCl_2$, and 0.002 mM $MgCl_2$ in HBSS) and allowed to adhere to plastic tissue culture plates for 1 hour. Non-adherent cells were removed by washing twice with HBSS and adherent cells (enriched B cells) were harvested by vigorous pipetting. $1 \times 10^5$ B cells and $2 \times 10^4$ mitomycin C treated CD40L-DAP3 transfected cells were cultured for 7 days in 96-well plates in 200 µl final volume complete medium (RPMI 1640) and 10% immunoglobulin free normal horse serum with 1 ng/ml recombinant huIL-2 (Peppro Tech Inc., Rocky Hill, N.J.) and 10% culture supernatant from cells transfected with library plasmids. Where indicated, pre-committed B cells and residual T cells were depleted by incubating panned B cells for 30 minutes on ice with 30 µl each of mouse anti-bovine IgA (Serotec, Raleigh, N.C.), mouse anti-bovine IgG1 (Serotec), mouse anti-bovine IgG2 (Serotec), and MM1A (anti-CD3 antibody, VMRD, Pullman, Wash.). The cells were washed 3 times with HBSS and sheep anti-mouse IgG Dynabeads (Dynal, Oslow, Norway) were added according to the manufacturer's instructions. The B cells were then placed in a magnetic field and the non-adherent cells removed. These cells were next incubated on ice for 30 minutes with biotinylated goat anti-bovine IgM (Kirkegard and Perry (KPL), Gaithersburg, Md.), washed 3 times and streptavidin beads (Dynal) were added according to the manufacturer's instructions. The cells were placed on a magnetic field and the adherent cells ($IgM^+B$ cells) were harvested. All bioassays were performed in triplicate in 96-well Corning flat bottom plates.

Other reagents used in these studies were goat anti-bovine IgM (5 µg/ml, KPL) and porcine TGF-β (1 ng/ml, R & D Systems, Minneapolis, Minn.) that had been acid-activated according to the manufacturer's instructions. To neutralize TGF-β, pan-specific TGF-β antibody produced in rabbits (R&D Systems) was used at 15 μg/ml (the optimal concentration recommended by the manufacturer) to neutralize the biological activity of TGF-β1, pTGF-β1.2, pTGF-β2, TGF-β3, and raTGF-β5. Rabbit-anti bovine IgA-inducing-protein antibody (5 μg/ml) was generated by immunizing a subcutaneously implanted chamber in a rabbit with IgA-inducing peptide (Office of Lab Animal Medicine, University of Missouri-Columbia) (Clemons et al., 1992a) and protein-A purifying Ig from the antiserum. The antiserum was filter sterilized prior to use. Filter sterilized, protein-A purified pre-immune rabbit serum (5 μg/ml and 15 μg/ml) was used for isotype controls.

Enzyme-Linked Immunosorbant Assay (ELISA)

Assessment of IgM, IgG, and IgA in culture supernatant was done by a sandwich capture ELISA in triplicate as described in Clemons et al. (1992a) and Clemons et al. (1992b). Briefly, Immulon II 96-well U bottom plates (Dynatech, Chantilly, Va.) were coated overnight at 4° C. with unlabeled affinity purified goat anti-bovine IgM (μ) (KPL), goat anti-bovine IgG(γ) (KPL), or goat anti-mouse IgG(γ) (KPL), respectively. Plates were then washed 3 times with phosphate buffered saline-solution (pH 7.2, PBS) and blocked with 10% normal horse serum (Gibco-BRL) in PBS for 1 hour at 37° C. Plates were again washed 3 times in PBS and IgA capture plates were incubated for 1 hour at 37° C. with monoclonal mouse-anti bovine IgA (Serotec), followed by washing. Undiluted sample supernatant (unless otherwise indicated) was then added in triplicate wells and plates were incubated for 1 hour at 37° C. Dilutions of purified bovine IgM (Sigma), bovine IgG (Sigma), or bovine IgA (partied from bovine colostrum using a mouse-anti-bovine IgA column) were used as standards in triplicate wells to quantify sample immunoglobulin. After washing, plates were incubated with alkaline phosphatase-labeled goat anti-bovine IgM(μ), IgG (γ) or IgG (H+L) (KPL) for 1 hour. Plates were then washed and incubated with a p-Nitrophenylphosphate Phosphatase Substrate Kit (KPL) according to the manufacturer's instructions. Concentrations of immunoglobulin were determined by linear regression relative to known standards (Clemons et al., 1992b). Results are depicted as the mean and standard error for triplicate cultures for each condition. Results are given in $OD_{410}$ or ng/ml as indicated.

DNA Sequencing

DNA was sequenced at the DNA core facility at the University of MO-Columbia using the Big Dye Chemistry Sequencing Kit (Perkin Elmer, Foster City, Calif.) on an Applied Biosystems 377 DNA Sequenator (Perkin Elmer).

RT-PCR

Total RNA was extracted from bovine tissue using a commercially available RNA extraction kit (TrZOL Reagent, Gibco-BRL). RT-PCR was performed according to the manufacturer's instructions (Perkin Elmer) with 1 ng of template using the following primers: IgA inducing protein (IGIP) sense 5'-GGG TGT AAT ATA ACC ATT CT -3' (SEQ ID NO:1) and IGIP antisense 5'-GGT ATT GAA CAA ACT CAA GCC -3' (SEQ ID NO:2). Housekeeping gene G3PDH was used as a positive control with the following primers: G3PDH sense 5'-GAG AAA CCT GCC-3' (SEQ ID NO:3) and G3PDH antisense 5'-TCG CTG TTG AAG TCG-3' (SEQ ID NO:4). Controls without reverse transcriptase were included to monitor potential amplification of low levels of contaminating genomic DNA. RT-PCR amplification conditions were as follows: reverse transcription at 42° C. for 15 minutes for 1 cycle, denaturation at 95° C. for 1 minute, annealing al 46° C. for 1 minute, and extension at 72° C. for 1 minute for 40 cycles.

Peptide Generation

Peptide was synthesized using standard fluorenmethloxycarbonyl (fmoc) chemistry on an Applied Biosystems 432 Peptide Synthesizer at the University of Missouri-Columbia, Department of Molecular Microbiology and Immunology. The peptide sequence was as follows: $NH_2$-Gly-Asn-Ser-Pro-Cys-Gly-Asn-Gln-Ala-Asn-Val-Leu-Cys-Ile-Ser-Arg-Leu-Glu-Phe-Val-Gln-Tyr-Gln-Ser-Cys-COOH (SEQ ID NO:16).

Results

Library Screening

To identify IgA switch factors, a cDNA expression library derived from bovine GALT tissue was screened using the following protocol (FIG. 1). Pools of library plasmids were transfected into BNLSV A.8 cells and the culture supernatant was collected after 72 hours and centrifuged to remove cells. Bioassays followed by ELISA were used to determine if the supernatant contained protein(s) that induced IgA production. In the bioassay, peripheral blood B cells were stimulated with 10% supernatant, CD40L-DAP3 cells and rhuIL-2 for 7 days. The supernatant from the bioassay was then tested by ELISA for secreted bovine IgM, IgG, and IgA. The plasmids from the pool that induced the highest IgA production were then further subdivided into 4 pools, using four 1 μl aliquots of the original pool. The plasmid aliquots were transformed into E. coli and grown up in media to increase the quantity of plasmids. The plasmids were isolated from the E. coli and transfected to begin a new round of screening.

Isolation of Individual Clone Which Induces IgA

After multiple rounds of library screening, an individual clone was isolated whose supernatant induced a two-fold increase in IgA production by B cells stimulated via CD40 and IL-2 compared to B cells stimulated via CD40 and IL-2 alone (Table I). B cell production of IgM and IgG were also slightly enhanced by clone supernatant.

TABLE I

Quantification of immunoglobulin induced by clone supernatant[a]

| | B cell stimulation | Concentrations in ng/ml | |
|---|---|---|---|
| | | IgA | Standard error |
| Exp 1 | media | 156 | 71 |
| | CD40L + IL2 | 1051 | 91 |
| | 10% supernatant + CD40L + IL2 | 2217 | 64 |
| Exp 2 | media | 147 | <30 |
| | CD40L + IL2 | 1156 | <30 |
| | 10% supernatant + CD40L + IL2 | 2246 | 43 |

[a]Quantification of IgA produced by B cells stimulated with clone 2 supernatant is in units of ng/ml. In each experiment, clone 2 DNA was transfected and the supernatants used in subsequent bioassays. In both experiments, B cells stimulated with clone 2 supernatant + CD40L + IL2 produced approximately twice as much IgA as B cells stimulated with CD40L + IL2 alone. Results are depicted as the mean and standard error for triplicate cultures for each condition.

DNA and Amino Acid Sequence of Clone 2

After confirming that the clone supernatant induced IgA production, the insert in the plasmid (clone 2 DNA) was sequenced (FIG. 2). Blast searches (Altschul et al., 1997) with the nucleotide sequence showed that clone 2 had no match with genes of assigned function. Clone 2 DNA was 96% homologous with a region on human chromosome 5 with unassigned function (FIG. 3) (Westbrook et al., 1990).

Homology with the sequence from human chromosome 5 is of considerable interest, because this chromosome contains genes for several cytokines including IL-3, IL-4, IL-5, IL-13 and GM-CSF (Marra et al., 1996). The clone nucleotide sequence of the insert was 92% homologous with an expressed sequence tagged (EST) mouse cDNA clone from mucosal lymph node tissue (FIG. 3) (Zan et al., 1998). The nucleotide sequence of clone 2 was translated, with the predicted longest complete open reading frame being 47 amino acids in length (FIG. 2). This amino acid sequence was 94% homologous with the amino acid sequence of a region on human chromosome 5 and approximately 91% homologous with the mouse cDNA lymph clone mentioned above (FIG. 3).

The product encoded by the insert DNA was named Immunoglobulin A-Inducing Protein (IGIP). The amino acid sequence of bovine IGIP is predicted to have a molecular weight of 5.1 KD and contains a signal sequence with a predicted cleavage site between amino acids 23–24 (Expert Protein Analysis System, Swiss Institute of Bioinformatics, Geneve, Switzerland).

IGIP Peptide and Antibody Bioassay Results

A peptide corresponding to IGIP amino acids 24–47 with an additional Cys on the carboxy terminus was generated. This peptide was used to generate a rabbit-anti bovine IGIP antibody (Clemons et al., 1992a). The peptide was used in bioassays to determine if it could directly induce IgA. When B cells were stimulated with CD40L+IL-2+ a range of concentrations (5 μg to 0.01 μg) of IGIP peptide, no increase in IgA production was observed (data not shown). There are a number of potential reasons the peptide did not induce IgA in bioassays. One possible reason is that the IGIP protein has potential N- and O-linked glycosylation sites, which would not be glycosylated in the synthetic peptide. Additionally, differences in protein folding could influence the peptide's activity.

The rabbit-anti bovine IGIP antibody was employed in bioassays to determine if it could inhibit the IGIP activity in supernatant from clone 2 transfected cells. Rabbit anti-bovine IGIP antibody blocked IgA induction from B cells stimulated with CD40L+IL-2+ supernatant from clone 2 transfected cells (Table II). This observation suggested that the amino acid sequence used to derive the synthetic peptide is the same amino acid sequence coding for the protein produced by clone 2 transfected cells.

TABLE II

Rabbit-anti-bovine IGIP antibody blocks IgA induction of B cells stimulated with IGIP supernatant.[a]

| | | Concentrations in ng/ml | | | | | |
|---|---|---|---|---|---|---|---|
| | B cell stimulation | IgA | s.e. | IgM | s.e. | IgG | s.e. |
| Exp 1 | CD40L + IL2 | 2044 | 159 | 1896 | 84 | 274 | 78 |
| | Media | <30 | | 248 | <30 | 66 | <30 |
| | 10% supernatant + CD40L + IL2 | 4582 | 271 | 2564 | 215 | 348 | <30 |
| | 10% supernatant + anti-IGIP + CD40L + IL2 | 849 | 104 | 389 | 37 | <30 | |
| | 10% supernatant + rabbit Ig + CD40L + IL2 | 3084 | 98 | 1906 | 245 | 305 | <30 |
| Exp 2 | CD40L + IL2 | 334 | 40 | 1530 | 185 | 152 | 19 |
| | Media | <30 | | <30 | | <30 | |
| | 10% supernatant + CD40L + IL2 | 1326 | 246 | 1418 | 98 | 222 | 63 |
| | 10% supernatant + anti-IGIP + CD40L + IL2 | | | 758 | <30 | <30 | |
| | 10% supernatant + rabbit Ig + CD40L + IL2 | 854 | <30 | 742 | 86 | 170 | 7 |

[a]Rabbit anti-IGIP antibody inhibits IgA induction from B cells stimulated with CD40L + IL2 and IGIP supernatant. Immunoglobulin concentrations are in units of ng/ml. Results are depicted as the mean and standard error for triplicate cultures for each condition. Concentrations of each isotype were determined by linear regression relative to known standards.

Comparison of IGIP and TGF-β in Stimulating B Cells

Because TGF-β is an important inducer of IgA, the effect of IGIP supernatant (crude supernatant containing IGIP from clone 2 transfected cells) and TGF-β when used alone or in combination in bioassays (Table III) was examined. B cells stimulated with IGIP supernatant had higher IgA (relatively 2 fold), IgG (less than 2 fold), and IgM (less than 2 fold) production than B cells stimulated with CD40L+IL-2 alone. B cells stimulated with TGF-β had less IgA production than B cells stimulated with CD40L+IL-2 or with IGIP supernatant+CD40L+IL-2 (the concentration of TGF-β used in the bioassay was selected because it had been shown to be optimal for IgA induction by bovine B cells stimulated through CD40 and anti-IgM). When B cells were stimulated with IGIP supernatant and TGF-β together, there was an increase in IgA (less than about 1 fold), but not as great as with IGIP supernatant alone. Importantly, the studies described above indicate that while TGF-β does not induce IgA production under conditions of B cell stimulation via CD40, IGIP is capable of inducing IgA production under these conditions.

TABLE III

Effects of TGF-β and IGIP supernatant on IgA induction.[a]

| | | Concentrations in ng/ml | | | | | |
|---|---|---|---|---|---|---|---|
| | B cell stimulation | IgA | s.e. | IgM | s.e. | IgG | s.e. |
| Exp 1 | CD40L + IL2 | 163 | <30 | 966 | 34 | 981 | 55 |
| | Media | <30 | | <30 | | <30 | |
| | 10% supernatant + CD40L + IL2 | 2214 | 145 | 1356 | 47 | 1059 | 32 |
| | TGF-β + CD40L + IL2 | 62 | <30 | 711 | 32 | 903 | <30 |
| Exp 2 | CD40L + IL2 | 2044 | 159 | 3772 | 84 | 548 | 78 |
| | Media | <30 | | 248 | <30 | 66 | <30 |
| | 10% supernatant + CD40L + IL2 | 4582 | 271 | 5128 | 215 | 696 | <30 |
| | TGF-β + CD40L + IL2 | 1552 | 400 | 3188 | 41 | 384 | 37 |
| | 10% supernatant + TGF-β + CD40L + IL2 | 2415 | 169 | 1929 | 45 | 360 | <30 |
| Exp 3 | CD40L + IL2 | 672 | <30 | 336 | <30 | 46 | <30 |
| | Media | <30 | | <30 | | <30 | |
| | 10% supernatant + CD40L + IL2 | 1646 | <30 | 440 | <30 | 62 | <30 |
| | TGF-β + CD40L + IL2 | 372 | <30 | 340 | 50 | 182 | <30 |
| | 10% supernatant + TGF-β + CD40L + IL2 | 1084 | <30 | 420 | 76 | 100 | <30 |

TABLE III-continued

Effects of TGF-β and IGIP supernatant on IgA induction.[a]

| B cell stimulation | Concentrations in ng/ml | | | | | |
|---|---|---|---|---|---|---|
| | IgA | s.e. | IgM | s.e. | IgG | s.e. |
| 10% supernatant + anti-TGF-β + CD40L + IL2 | 664 | <30 | 560 | 38 | <30 | |
| TGF-β + anti-TGF-β | 653 | 80 | 520 | 31 | <30 | |

[a]B cells were stimulated with CD40L + IL2, and either IGIP supernatant, TGF-β, or a combination of the two. Additionally anti-TGF-β was used to block TGF-β in cultures. Data from 3 separate experiments are shown and with each experiment being repeated at least 2 times. Results are depicted as the mean and standard error for triplicate cultures for each condition. Concentrations of each isotype were determined by linear regression relative to known standards.
Results are in units of ng/ml.

Collectively, these results suggested that IGIP could be working in a TGF-β independent manner. However, studies have shown that human and mouse IgM$^+$ IgD$^+$B cells produce endogenous TGF-β when stimulated via CD40 (Snapper et al., 1993). Because TGF-β can be produced by activated B cells, it is possible that TGF-β was present in the cultures of B cells stimulated with CD40L+IL-2+IGIP supernatant. To begin to address this question, pan-specific anti-TGF-β (15 μg/ml) antibody or rabbit Ig (15 μg/ml) was used in co-culture with IGIP supernatant+B cells+CD40L+ IL-2 (Table III). IgA induction by B cells stimulated with a combination of IGIP supernatant and anti-TGF-β was less than that of B cells stimulated with IGIP containing supernatant alone. B cells stimulated with a combination of control rabbit Ig and IGIP containing supernatant had decreased immunoglobulin production for IgA as well (Table III), but the decrease in IgA was not as great as that seen with anti-TGF-β. Overall, these studies suggest that the induction of IgA by B cells stimulated with IGIP-containing supernatant may be dependent on endogenous TGF-β, because the decrease in IgA with the control is less than the decrease in IgA with anti-TGF-β. It is important to emphasize that TGF-β is ineffective at inducing IgA when B cells are stimulated via CD40 alone, whereas IGIP-containing supernatant can induce IgA production by B cells stimulated via CD40.

TABLE IV

IgA is induced by both IGIP supernatant and TGF-β in B cells stimulated through CD40 and BCR[a]

| | B cell stimulation | Concentrations in ng/ml | | | | | |
|---|---|---|---|---|---|---|---|
| | | IgA | s.e. | IgM | s.e. | IgG | s.e. |
| Exp 1 | CD40L + IL2 | 2024 | 185 | 3144 | <30 | 652 | <30 |
| | Media | <30 | | 248 | <30 | 66 | <30 |
| | 10% supernatant + CD40L + IL2 | 5356 | 164 | 5836 | <30 | 886 | <30 |
| | 10% supernatant + TGF-β + CD40L + IL2 | 2722 | <30 | 3276 | 52 | 608 | 52 |
| | TGF-β + CD40L + IL2 | 1960 | 153 | 3286 | 41 | 396 | 41 |
| | TGF-β + biotinylated anti-IgM + CD40L + IL2 | 4886 | 1208 | 556 | <30 | 1482 | 71 |
| | TGF-β + _anti-IgM + CD40L + IL2 | 3448 | 452 | 106 | <30 | 974 | 104 |
| Exp 2 | anti-IgM + CD40L + IL2 | 310 | <30 | 2239 | 300 | 935 | 112 |
| | Media | <30 | | 43 | <30 | <30 | |
| | 10% supernatant + anti-IgM + CD40L + IL2 | 1034 | <30 | 2356 | 125 | 805 | 110 |
| | TGF-β + anti-IgM + CD40L + IL2 | 3171 | 93 | 1844 | 290 | 542 | <30 |
| | 10% supernatant + anti-TGF-β + anti-IgM + CD40L + IL2 | 276 | 43 | 2680 | 272 | 1002 | 297 |
| | TGF-β + anti-TGF-β + anti-IgM + CD40L + IL2 | 72 | <30 | 1674 | 143 | 1272 | 157 |
| | anti-TGF-β + anti-IgM + CD40L + IL2 | 95 | 36 | 1684 | 93 | 605 | 43 |

[a]B cells stimulated with TGF-β + CD40L + IL2 have decreased IgA levels. However B cells stimulated though CD40 and BCR have increased IgA when cultured with TGF-β. In experiment 1, B cells purified by panning were simulated with CD40L and the BCR was cross-linked using goat anti-bovine IgM as indicated. In experiment 2, panned B cells were depleted of IgA, IgG1, IgG2, and T cell using negative selection. These cells were 70% IgM$^+$B cells asdetermined by flow cytometric analysis. These B cells were then positively selected using biotinylated goat-anti-bovine IgM. Data above is representative of repeated experiments. Results are depicted as the mean and standard error for triplicate cultures for each condition. Concentrations of each isotype were determined by linear regression relative to known standards.

There are two mechanisms by which IGIP may be influencing IgA production. First, IGIP might be a switch factor controlling differentiation of IgM$^+$ B cells to IgA$^+$B cells. Alternatively, IGIP could be a terminal differentiation factor, causing IgA pre-committed B cells to become high rate secretors of IgA. To address this issue, a more defined starting population of IgM$^+$B cells was stimulated with IGIP containing supernatant (Table IV, experiment 2). In these experiments panned B cells were negatively depleted of T cells, IgG$_1$, IgG$_2$, and IgA expressing cells. These cells were approximately 70% IgM$^+$B cells as analyzed by flow cytometry (Table IV). The resulting B cell population was then further purified by positively selecting for B cells expressing IgM using biotinylated goat-anti-bovine IgM antibody. Under conditions of B cell stimulation via CD40 and anti-IgM, IGIP containing supernatant again induced IgA production from B cells. This finding suggest that IGIP might be regulating isotype switching, although it is not possible to eliminate the potential role of IGIP as a terminal differentiation factor expanding residual pre-committed IgA B cells in the starting populations. Presently, IgA switch region sequences are unknown.

To investigate the role of IGIP in comparison with TGF-β on isotype switching in B cells that were stimulated through both CD40 and the BCR (Table IV), panned B cells were stimulated with CD40L with or without anti-IgM antibody (experiment 1 in Table IV). TGF-β induced IgA production from B cells stimulated through both CD40 and BCR together; however, TGF-β decreased IgA production from B cells stimulated through only CD40. In the same experiment, IGIP induced IgA production from B cells stimulated via CD40 alone. In Table IV experiment 2, B cells which have undergone anti-IgM cross-linking were cultured with CD40L+IL-2 and IGIP supernatant or TGF-β. Under these stimulation conditions, IGIP supernatant induced IgA production approximately 3-fold over that of B cells stimulated via CD40L+anti-IgM+IL-2. TGF-β induced IgA production 10 fold over the level of IgA produced by B cells stimulated via CD40L+anti-IgM+IL-2 alone. Thus, under dual stimulation conditions, TGF-β appears to be a more effective inducer of IgA relative to IGIP. However, IGIP is able to induce IgA production from dual stimulated B cells as well as CD40 stimulated B cells.

Tissue Expression of IGIP

To investigate IGIP expression in tissue, RT-PCR was performed on total RNA extracted from bovine tissues. IGIP mRNA was present in PP, spleen, thymus, liver, and mesenteric lymph node from three different animals (FIG. 4). Nasal epithelium was negative for IGIP mRNA (data not shown). Positive controls with a housekeeping gene G3PDH for loading and quality of RNA and negative controls with no reverse transcriptase added prior to PCR were done in these experiments. Based upon mRNA, this data suggest that IGIP is expressed in spleen, thymus, liver, mesenteric lymph node and at lower levels in the PP.

Use of IGIP as a Mucosal Adjuvant

To determine whether IGIP was useful as a mucosal adjuvant, SCID-bovine mice (see Denny et al., 1996; Smith et al., 1999) were immunized with whole bovine virus diarrhea virus (BVDV-type 1) in adjuvant containing various isoforms of IGIP. SCID-bovine mice were immunized intraperitoneally with approximately 10 micrograms of whole virus antigen at day 0 and day 28. IGIP was administered at 10 micrograms. Plasma was collected at days 0, 14 and 35 and pooled from individual mice by treatment group for analysis. Five animals were immunized per treatment group and pooled using equal volumes from each subject. Prevaccination plasma samples were negative for BVDV-specific antibody for all treatment groups. As shown in Table V, BVDV-specific antibodies were only detected in the plasma of SCID-bovine mice immunized with a combination of IGIP and BVDV.

TABLE V

| immunogen | adjuvant | detection of virus specific antibody[a] |
|---|---|---|
| buffer | saponin emulsion only | no |
| BVDV | saponin emulsion only | no |
| BVDV | saponin emulsion + IGIP (disulfide)[b] | no |
| BVDV | saponin emulsion + IGIP[b] | yes |

[a]Direct binding by dot blot and chemiluminescence detection (ECL + kit, Amersham)
[b]Peptide containing a disulfide bridge or absent between two conserved cysteine residues within the predicted open reading frame of the protein Discussion In the present studies, IGIP was identified as a novel factor regulating IgA production by bovine B cells, with homologs in humans and mice. IGIP was shown to induce IgA secretion from B cells stimulated via CD40 alone or a combination of CD40 and BCR signaling. Importantly, IGIP is able to induce IgA production from B cells under stimulation conditions in which TGF-β cannot. Finally, IGIP might be expressed in a variety of different tissues, including both lymphoid and non-lymphoid tissues.

The identification of homology between bovine IGIP and a gene on human chromosome 5 may be of immunological significance. Chromosome 5 contains genes for several cytokines known to affect lymphocyte differentiation and proliferation. Also, IGIP may be present in multiple species, since homologs have been found in both mouse and human. Therefore, the findings described herein may be of broader application than to isotype regulation in cattle alone.

IGIP induces IgA production by B cells stimulated via CD40 or a combination of CD40 and anti-IgM. There are at least two mechanisms by which IGIP might be regulating IgA production. First, IGIP might be a switch factor influencing IgM$^+$ B cells to become IgA$^+$ B cells. Alternatively, IGIP could be a terminal differentiation factor, causing pre-committed IgA cells to become high rate secretors of this isotype. As described above, IGIP induced IgA production from B cells depleted of cells pre-committed to IgA, IgG$_1$ and IgG$_2$ synthesis, suggesting that IGIP could be acting as an isotype switch factor (Table IV). However, even though the cell populations were depleted of B cells expressing IgA on the surface, the B cells could still be contaminated with some residual pre-committed IgA B cells (as suggested by IgA production from B cells stimulated with CD40L+IL-2 alone). Therefore, IGIP could be a terminal differentiation factor acting on pre-committed cells to induce differentiation into plasma cells. Alternatively, IGIP could be both a switch and terminal differentiation factor, as shown with other cytokines, for example, IL-10 in humans (McIntyre et al., 1999).

Additionally, IGIP supernatant seems to slightly induce IgG and IgM production by B cells, therefore, IGIP might be a general enhancer of production for multiple immunoglobulins in cattle (in addition to its role in IgA induction). In cattle, TGF-β enhances IgA and IgG$_2$, and IGIP could also regulate more than one isotype in a similar manner. Additionally in cattle, IL-2 enhances immunoglobulin production of multiple isotypes and IGIP might have a similar function (data not shown).

The studies described herein demonstrate that B cells stimulated via CD40+IL-2 have decreased IgA production in the presence of exogenous TGF-β. This decrease in IgA could be explained by a dose-dependency in the effects of TGF-β on B cells stimulated via CD40. Addition of TGF-β to cultures, which already have endogenous TGF-β, might cause the final concentration of TGF-β to become so high that it is suppressive to B cells stimulated via CD40 alone. TGF-β is known to have inhibitory effects on lymphocyte proliferation, differentiation, and progression through the cell cycle (McIntyre et al., 1995, Ehrhardt et al., 1992). If high concentrations of TGF-β were suppressive to B cells, upregulation of survival factors by IGIP could rescue the B cells allowing them to produce IgA. This hypothesis is consistent with the finding herein that TGF-β decreases IgA production by B cells stimulated via CD40, but IgA induction is restored by the presence of IGIP-containing supernatants. This explanation is supported by the fact that IL-10 not only enhances B cell survival by inducing the anti-apoptotic factor Bcl-2, but also enhances IgA secretion by human B cells stimulated via anti-CD40 antibody in the presence of TGF-β (VanVlasselaer et al., 1992).

Because stimulation of B cells via different receptor molecules can effect the phenotype of B cells, the effect of IGIP supernatant under conditions of dual (CD40 and BCR) or single (CD40) B cell stimulation was examined. Under conditions of dual stimulation, IGIP supernatant induces IgA production by B cells, but TGF-β induces even higher levels of IgA production (Table IV). This data differs from the results of B cells stimulated by CD40 alone, in which IGIP caused the greatest induction of IgA and TGF-β decreased IgA production (Table III). Therefore, under conditions of dual stimulation, TGF-β is more effective at inducing IgA production than IGIP. However, under conditions of single stimulation (CD40 alone), IGIP is able to induce IgA production, but TGF-β decreases IgA production. Thus, IGIP and TGF-β may use different signaling pathways to regulate IgA or the genes for IGIP and TGF-β may be controlled by different stimulation conditions.

B cells stimulated with IGIP supernatant have increased IgA, however, B cells stimulated with IGIP supernatant and anti-TGF-β have decreased IgA, as well as IgM and IgG. B cells stimulated with control rabbit Ig and IGIP supernatant have decreased IgA production as well, but the decrease is less than that of B cells stimulated with IGIP supernatant and anti-TGF-β (Table III). Hence, IGIP may be dependent on endogenous TGF-β for IgA induction. Endogenous TGF-β might be needed for upregulation of the receptor(s) for IGIP. Without endogenous TGF-β, B cells might not upregulate the IGIP receptor, so IGIP would not be able to induce IgA production.

Figure 5:
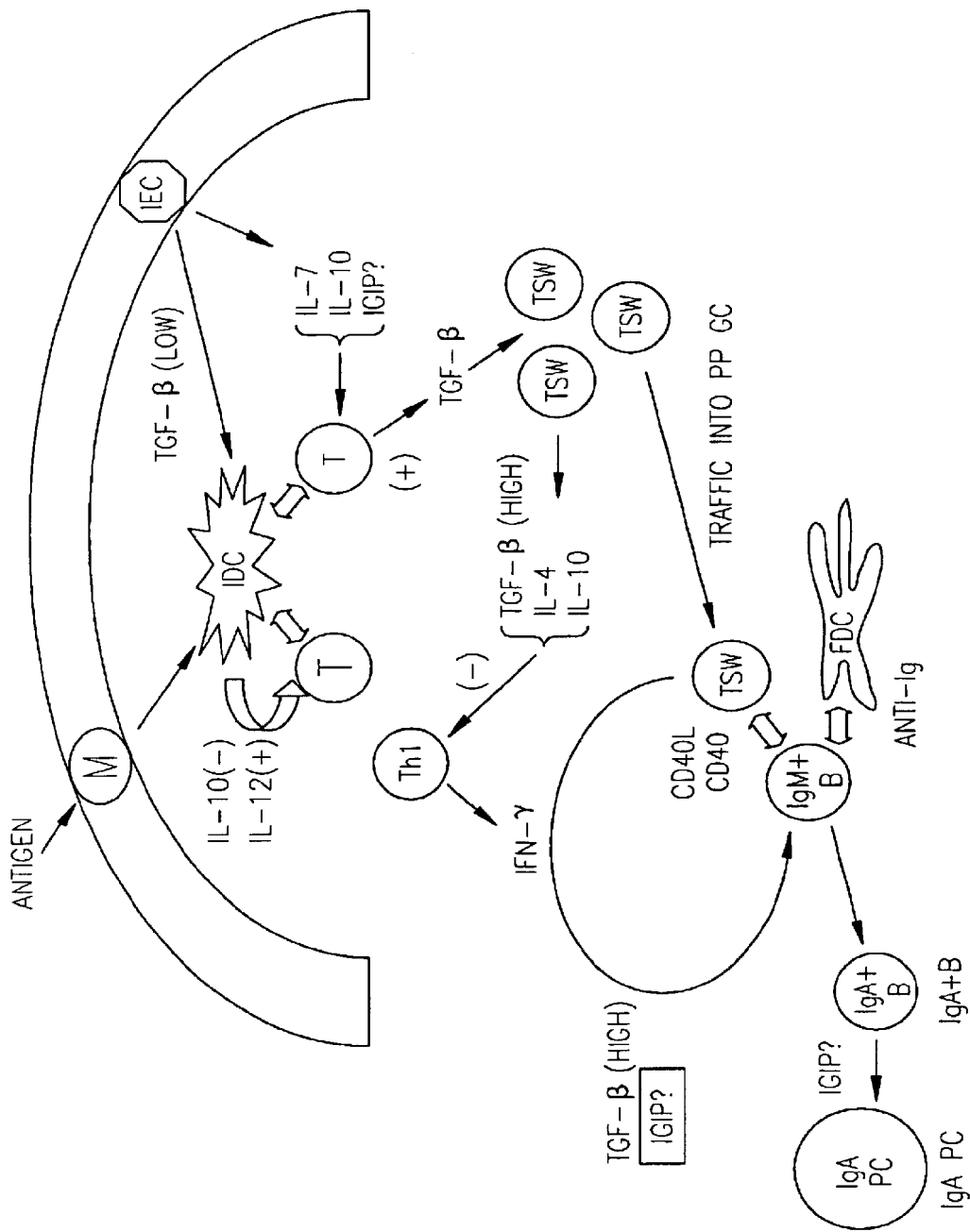
FIG. 5. Hypothetical model showing role of IGIP in GALT immune response (adapted from Kehrl et al., 1986). Antigen is taken up by M cells and transported into the PP. IDCs (intradigitating dendritic cells) immediately take up antigen and migrate to T cell areas of the PP where they present antigen to T cells, which causes the T cells to become activated. Initially, the activated T cells produce Th1 cytokines characterized by IFN-γ. However, the Th1 response is short-lived because of Th2 cytokines, the TGF-β rich environment of the PP, and possibly IL-10 production by the IDCs. At the same time that M cells are transporting antigen into the PP, intraepithelial cells (IEC) are secreting a wide variety of cytokines like TGF-β, IL-7, IL-10, and likely IGIP. TGF-β induces the IDC to interact with the T cell in such a way that the T cells begin to secrete TGF-β. These TGF-β secreting T cells differentiate into switch T cells (TSW). Switch T cells express CD40L, secrete high amounts of TGF-β, and skew isotype switching of B cells to IgA. IL-7 and IL-10 are also known to enhance differentiation of T cells into TSW. It is possible that IGIP may also act upon T cells causing them to produce TGF-β and to differentiate into TSW. The TSW secrete Th2 cytokines that shut down the Th1 response. TSW migrate into the germinal center where they interact with B cells in such a way that isotype switching is skewed to IgA. The switch T cells produce high levels of TGF-β that may be responsible for isotype skewing to IgA in PP germinal centers. However, because high concentrations of TGF-β are inhibitory to the B cell, a second signal derived from the follicular dendritic cells or T cell derived cytokines might be needed to sustain B cell viability. IGIP may be produced by TSW and act upon B cells to sustain their viability in addition to enhance isotype switching to IgA. Alternatively, if B cells are only stimulated via CD40, this B-T cell interaction may cause TSW to produce mainly IGIP, which induces the B cells to differentiate into IgA B cells. Differences in TSW activation, antigens, and other cytokines in the environment may regulate the production of TGF-β, IGIP, or a combination of both by TSW. After B cells have undergone isotype switching, IGIP could be produced by T cells (or other cells) in mucosal effector sites like the lamina propria inducing terminal differentiation into IgA plasma cells.

FIG. 5 shows a model for the role of IGIP in IgA regulation of GALT. As illustrated in the model, IGIP could be influencing IgA production at multiple steps in the mucosal immune response. IGIP could be either a switch factor, a terminal differentiation factor, or possibly both.

In summary, a novel regulatory factor for IgA, IGIP, was identified, which has homologs in mice and humans. IGIP induces IgA production by B cells stimulated via CD40, a condition in which TGF-β does not induce IgA, and induces IgA production from B cells stimulated via a combination of anti-IgM and CD40. However TGF-β is more efficient at inducing IgA than IGIP under the latter conditions. Thus, IGIP may be either a terminal differentiation and/or a switch factor.

References

Abdallah et al., *Biol. Cell,* 85:1 (1995).
Ada, In: *Fundamental Immunology,* 2$^{nd}$ ed., Raven Press Ltd., N.Y., pp. 985–1030 (1989).
Adelman et al., *DNA,* 2, 183 (1983).
Almquist, R. G. et al., *J. Med. Chem.* 23:1392–1398 (1980).
Altschul et al., *Nucleic Acids Res.* 25:3389 (1997).
Bavaay and Merrifield, "The Peptides," eds. E. Gross and F. Meienhofer, Vol. 2, pp. 3–285 (Academic Press, 1980).
Brandtzaeg et al., *Gastroenterology,* 97:1562 (1989).
Clark-Lewis et al., *Meth. Enzymol.,* 287, 233 (1997).
Clemons et al., *Lab Anim Sci.* 42:307 (1992a).
Clemons et al., *Lab. Anim. Sci.* 42:307 (1992b).
Coffman et al., *J. Exp. Med.* 170:1039 (1989).
Crea et al., *Proc. Natl. Acad. Sci. U.S.A.,* 75:5765 (1978).
Dayhoff, M. O., in Atlas of Protein Sequence and Structure, volume 5, National Biomedical Research Foundation, pp. 101–110 and Supplement 2 to this volume, pp. 1–10 (1972).
Delacroix, D. L., and J. P. Vaerman, 1985. "The human immunoglobulin A system. Its vascular compartment". European Medical Press, Brugge, Belgium.
Denny et al., *Lab. Animal Sci.,* 46:48 (1996).
Donnelly et al.,*Ann. N.Y. Acad. Sci.,* 772:40 (1995).
Ehrhardt et al., *J. Immunol.* 148:3830 (1992).
Erhardt et al., *J. Immunol.* 157:1397 (1996).
Erlich, ed., *PCR Technology,* Stockton Press, NY (1989).
Eskola et al., *Lancet,* 1:1184 (1985).
Estes et al., *Immunol.* 95:604 (1998).
Evans et al., *J. Med. Chem,* 30:1229 (1987).
Fauchere, *Adv. Dru Res.,* 15:29 (1986).
Fayette et al., *J. Ex. Med.* 185(11):1909 (1997).
Goeddel et al., *Nucleic Acids Res.* 8:4057 (1980).
Hann., *J. Chem. Soc.* Perkin Trans I 307 (1982).
Holladay et al., *Tetrahedron Lett.* 24:4401 (1983).
Hruby, *Life Sci.* 31:189(1982).
Hudson et al., *Int. J. Pept. Prot. Res.* 14:177 (1979).
Islam et al., *Int. Immunol.* 3:1099 (1991).
Jameson et al. *Nature* 368:744 (1994).
Jennings-White et al., *Tetrahedron Lett.* 23:2533 (1982).
Kehrl et al., *J. Immunol.* 146:4016 (1991).
Kehrl et al., *J. Immunol.* 137:3855 (1986).
Kim et al., *J. Immunol.* 160:1198 (1998).
Kim et al., *J. Immunol.* 145:3773 (1990).
Kimata et al., *Blood* 85:2098 (1995).
Kimata et al., *Eur. J. Immunol.* 9:2262 (1994).
Kimmerly et al., Genbank (NCBI) assession # AC005575
Lawn et al., *Nucleic Acids Res.* 9:6103 (1981).
Lebman et al., *J. Exp. Med.* 168:853 (1990).
Lin et al., *J. Immunol.* 149:2914 (1992).
Marra et al., , Genbank (NCBI) accession # AA204132.
McIntrye et al., In "Handbook of Mucosal Immunology". (second ed.) pg 319–356, Academic Press, New York (1999)
McIntyre et al., *J. Immunol.* 154:3156 (1995).
Meienhofer in "Hormonal Proteins and Peptides," ed.; C. H. Li, Vol. 2, pp. 48–267, Academic Press (1973).
Merrifield, *J. Am. Chem. Soc.,* 85:2149 (1963).
Molling, *J. Mol. Med.,* 75:242 (1997).
Morley, *Trends Pharm. Sci. pp.* 463–468 (1980).
Moses et al., *Cell* 63:245 (1990).
Mullis et al., *Cold Spring Harbor Symp. Quant. Biol.,* 51:263 (1987).
Needleman and Wunsch *J. Mol. Biol.* 48:443 (1970).
Pardoll et al., *Immunity,* 3:165 (1995).
Pearson and Lipman, *Proc. Natl. Acad. Sci. (U.S.A.)* 85:2444 (1988).
Sambrook et al., *Molecular Cloning: A Laboratory Manual,* Cold Spring Harbor, N.Y. (1989).
Severson et al., *Immunol. Lett.* 15:294 (1987).
Shpargo et al., *Int. Immunol.* 8:781 (1996).
Simmons et al., *Science,* 276:276 (1997).
Smith and Waterman, *Adv. Appl. Math.* 2:482 (1981).
Smith et al., *J. Leuk. Biol.,* 65:28 (1999).
Snapper et al., *J. Immunol.* 151(9):4625 (1993).
Sonada et al., *J. Ex. Med.* 170:1415 (1989).
Spatola et al., *Life Sci.* 38:1243 (1986).
Spatola, in "Chemistry and Biochemistry of Amino Acids, Peptides, and Proteins," B. Weinstein, eds. Marcel Dekker, New York, P. 267 (1983).
Spatola, Vega Data, Vol. 1, Issue 3, "Peptide Backbone Modifications" (1983)).
Stevenson et al., *Immunol. Rev.,* 145:211 (1995).
Stewart et al., *Solid Phase Peptide Synthesis,* W. H. Freeman Co., San Francisco (1969).
Van Vlasselae et al., *J. Immunol.* 148:2062 (1982).
Veber and Freidinger, TINS p. 392 (1985).
Viera et al., *Meth. Enzymol.,* 153:3 (1987).
Westbrook, C. A., *Human Genome News* 11:2(4) (1990).
Yang et al., *Mol. Med. Today,* 2:476 (1996).
Zan et al., *J. Immunol.* 161:5217 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: A primer

<400> SEQUENCE: 1
gggtgtaata taaccattct                                                    20

<210> SEQ ID NO 2
<211> LENGTH: 21
<212> TYPE: DNA
<213> ORGANISM: Artificial Sequence
<220> FEATURE:
<223> OTHER INFORMATION: A primer

<400> SEQUENCE: 2
ggtattgaac aaactcaagc c                                                  21

<210> SEQ ID NO 3
<211> LENGTH: 12
<212> TYPE: DNA
<213> ORGANISM: Artificial Sequence
<220> FEATURE:
<223> OTHER INFORMATION: A primer

<400> SEQUENCE: 3
gagaaacctg cc                                                            12

<210> SEQ ID NO 4
<211> LENGTH: 15
<212> TYPE: DNA
<213> ORGANISM: Artificial Sequence
<220> FEATURE:
<223> OTHER INFORMATION: A primer

<400> SEQUENCE: 4
tcgctgttga agtcg                                                         15

<210> SEQ ID NO 5
<211> LENGTH: 24
<212> TYPE: PRT
<213> ORGANISM: Bos taurus

<400> SEQUENCE: 5

Gly Asn Ser Pro Cys Gly Asn Gln Ala Asn Val Leu Cys Ile Ser Arg
 1               5                  10                  15

Leu Glu Phe Val Gln Tyr Gln Ser
            20

<210> SEQ ID NO 6
<211> LENGTH: 451
<212> TYPE: DNA
<213> ORGANISM: Bos taurus

<400> SEQUENCE: 6
ccaattatac agtagaatat cattaatttg cactggttgg ggaccccatt aagaatgctg         60
aattttgcca actaagaagt aagcaaatgc aatttaaaaa gtaaatttga gcattctgta       120
ttaaatctgt gcagctatta tcacatgaag aagcgcagtg tgtcgggctg taatataacc       180

```
atacttgctg ttgtgttctc ccatctcagt gctgggaact caccatgtgg aaaccaagca    240
aatgtgttgt gcatcagccg gcttgagttt gttcaatatc aaagctgaaa ctagcgaggt    300
ctgctgtact gcttattgaa gtattgtgat tctttaggc attgattctt aaaaaatata     360
tactgtaaca gtatactttg tacagattta aatttattt gaaaaaatg aaataaagta      420 ggcaaaaaaa taaaaaaaaa aaaaaaaaaa a                                    451
```

```
<210> SEQ ID NO 7
<211> LENGTH: 47
<212> TYPE: PRT
<213> ORGANISM: Bos taurus

<400> SEQUENCE: 7

Met Lys Lys Arg Ser Val Ser Gly Cys Asn Ile Thr Ile Leu Ala Val
  1               5                  10                  15

Val Phe Ser His Leu Ser Ala Gly Asn Ser Pro Cys Gly Asn Gln Ala
             20                  25                  30

Asn Val Leu Cys Ile Ser Arg Leu Glu Phe Val Gln Tyr Gln Ser
         35                  40                  45

<210> SEQ ID NO 8
<211> LENGTH: 47
<212> TYPE: PRT
<213> ORGANISM: homo sapien

<400> SEQUENCE: 8

Met Lys Lys Arg Ser Val Ser Gly Cys Asn Ile Thr Ile Phe Ala Val
  1               5                  10                  15

Met Phe Ser His Leu Ser Ala Gly Lys Ser Pro Cys Gly Asn Gln Ala
             20                  25                  30

Asn Val Leu Cys Ile Ser Arg Leu Glu Phe Val Gln Tyr Gln Ser
         35                  40                  45

<210> SEQ ID NO 9
<211> LENGTH: 47
<212> TYPE: PRT
<213> ORGANISM: mus musculus

<400> SEQUENCE: 9

Met Lys Lys Arg Ser Val Leu Gly Cys Asn Ile Thr Ile Phe Ala Val
  1               5                  10                  15

Met Phe Ser His Leu Ser Ala Gly Asn Ser Pro Cys Gly Asn Gln Ala
             20                  25                  30

Thr Val Leu Cys Ile Ser Arg Leu Glu Phe Val Gln Tyr Gln Ser
         35                  40                  45

<210> SEQ ID NO 10
<211> LENGTH:
<212> TYPE:
<213> ORGANISM:

<400> SEQUENCE: 10

00

<210> SEQ ID NO 11
<211> LENGTH: 413
<212> TYPE: DNA
<213> ORGANISM: homo sapien

<400> SEQUENCE: 11
```

```
aatatcatta atttgcactg tttggggacc ccatttaaga atgctgaatt ttgccaacta      60
agaagtaagc aaatgcaatt taaaaagtaa atttgagcat tctgtattaa atatgtgcag     120
ttattatcac atgaagaaac gcagtgtgtc gggctgtaat attaccatat ttgctgtcat     180
gttctcccat ctcagtgctg ggaaatcacc atgtggaaac caagcaaacg tgttgtgcat     240
cagccggctt gagtttgttc aatatcaaag ctgaaaacta gcgaggtctg ctgtactgct     300
tattgaagta ttgtgattat tttaggcatt gattcttaca aaatatatac tgtaacagta     360
tactttgtac agatttaaat tttatttgaa aaaatgaaat aaagtaggca aaa            413

<210> SEQ ID NO 12
<211> LENGTH: 381
<212> TYPE: DNA
<213> ORGANISM: mus musculus

<400> SEQUENCE: 12
attaatttgc actgtttggg gacccattta agaatgctga attttgccaa actaaaaagt      60
aagcaaatgc aatttaaaaa gtaaatttga gcattctgtg ttaaatatgt gcagttatta     120
tcatatgaag aagcgcagtg tgttgggctg taatataacc atatttgctg tcatgttctc     180
ccatctcagt gctgggaact caccatgtgg aaaccaagca accgtgttgt gcatcagccg     240
gcttgagttt gttcaatatc aaagctgaag ctagcgaggt ctgctgtact gcttattgaa     300
gtattgtgat tcttttaggc attggttctt acaaaatata tactgtaaca gtatactttg     360
tacagattta aattttattt g                                               381

<210> SEQ ID NO 13
<211> LENGTH: 24
<212> TYPE: PRT
<213> ORGANISM: Homo Sapien

<400> SEQUENCE: 13

Gly Lys Ser Pro Cys Gly Asn Gln Ala Asn Val Leu Cys Ile Ser Arg
  1               5                  10                  15

Leu Glu Phe Val Gln Tyr Gln Ser
                20

<210> SEQ ID NO 14
<211> LENGTH: 24
<212> TYPE: PRT
<213> ORGANISM: Mus musculus

<400> SEQUENCE: 14

Gly Asn Ser Pro Cys Gly Asn Gln Ala Thr Val Leu Cys Ile Ser Arg
  1               5                  10                  15

Leu Glu Phe Val Gln Tyr Gln Ser
                20

<210> SEQ ID NO 15
<211> LENGTH: 412
<212> TYPE: DNA
<213> ORGANISM: Bos taurus
<220> FEATURE:
<221> NAME/KEY: misc_feature
<222> LOCATION: (1)...(412)
<223> OTHER INFORMATION: n = A,T,C or G

<400> SEQUENCE: 15
aatatcatta atttgcactg gttggggacc ccattaagaa tgctgaattt tgccaactaa      60
```

```
-continued gaagtaagca aatgcaattt aaaaagtaaa tttgagcatt ctgtattaaa tctgtgcagc        120
tattatcaca tgaagaagcg cagtgtgtcg ggctgtaata taaccatact tgctgttgtg        180
ttctcccatc tcagtgctgg gaactcacca tgtggaaacc aagcaaatgt gttgtgcatc        240
agccggcttg agtttgttca atatcaaagc tgaaactagc gaggtctgct gtactgctta        300
ttgaagtatt gtgattcttt taggcattga ttcttaaaaa atatatactg taacagtata        360
ctttgtacag atttaaattt tatttgnnnn nnntgaaata aagtaggcaa aa               412

<210> SEQ ID NO 16
<211> LENGTH: 25
<212> TYPE: PRT
<213> ORGANISM: Artificial Sequence
<220> FEATURE:
<223> OTHER INFORMATION: A peptide corresponding to IGIP amino acids
      24-47 with an additional Cys on the carboxy terminus.

<400> SEQUENCE: 16

Gly Asn Ser Pro Cys Gly Asn Gln Ala Asn Val Leu Cys Ile Ser Arg
 1               5                  10                  15

Leu Glu Phe Val Gln Tyr Gln Ser Cys
            20                  25
```

What is claimed is:

1. An isolated and purified mammalian Immunoglobulin A Inducing Protein (IGIP) comprising a sequence having at least 95% amino acid sequence identity to SEQ ID NO:5 which induces Immunoglobulin A.

2. The IGIP of claim 1 which is bovine.

3. The IGIP of claim 1 which is human.

4. The IGIP of claim 1 which is murine.

5. The IGIP of claim 1 which comprises SEQ ID NO:5.

6. An isolated polypeptide having at least about 95% but less than 100% amino acid sequence identity to SEQ ID NO:5.

7. The IGIP of claim 1 which consists of SEQ ID NO:5.

8. An immunogenic composition comprising an immunogen and an effective adjuvant amount of the IGIP of any one of claims 1 to 6 or 7.

9. The immunogenic composition of claim 8 which is adapted for parenteral, subcutaneous, intramuscular, oral or intranasal administration to a mammal.

10. An isolated polynucleotide comprising a nucleic acid segment comprising SEQ ID NO:6.

11. An isolated polypeptide having at least 95% but less than 100% amino acid sequence identity to SEQ ID NO:7.

12. A method to enhance the immune response of a mammal to an immunogen, comprising: contacting a mammal with an immunogen and an amount of the IGIP polynucleotide of claim 11 effective to enhance the immune response of the mammal to the immunogen relative to the immune response of a corresponding mammal contacted with the immunogen but not the IGIP polynucleotide.

13. A method to enhance the immune response of a mammal to an immunogen, comprising: contacting a mammal with an immunogen and an amount of the IGIP of any one of claims 1 to 6 or 7 effective to enhance the immune response of the mammal to the immunogen relative to the immune response of a corresponding mammal contacted with the immunogen but not IGIP.

14. The method of claim 13 wherein the mammal is a bovine, guinea pig or mouse.

15. The method of claim 13 wherein the mammal is a human.

16. The method of claim 13 wherein the immunogen is a pathogen.

17. The method of claim 16 wherein the pathogen is a virus.

18. The method of claim 16 wherein the pathogen is a bacteria.

19. The method of claim 13 wherein the immunogen is an antigenic portion of a pathogen.

20. The method of claim 19 wherein the antigenic portion is a peptide.

21. The method of claim 19 wherein the antigenic portion comprises a carbohydrate.

22. An isolated and purified polypeptide comprising SEQ ID NO:5 or SEQ ID# 7.

23. The IGIP of claim 1 which induces IgA secretion in vitro.

24. The isolated polynucleotide of claim 11 wherein the mammalian IGIP induces IgA secretion in vitro.

25. The method of claim 13 wherein the contacting enhances immunogen-specific immunoglobulin production.

26. An isolated and purified peptide comprising a sequence with least 95% amino acid sequence identity to SEQ ID NO:5 or SEQ ID# 7.

27. The isolated and purified peptide of claim 26 which consists of SEQ ID NO:5.

* * * * *

UNITED STATES PATENT AND TRADEMARK OFFICE
CERTIFICATE OF CORRECTION

PATENT NO. : 6,930,167 B2
DATED : August 16, 2005
INVENTOR(S) : Estes et al.

It is certified that error appears in the above-identified patent and that said Letters Patent is hereby corrected as shown below:

Column 41,
Line 38, after "least" delete "about".
Line 38, after "95%" insert -- , --.
Line 54, delete "claim 11" and insert -- claim 10 --.

Column 42,
Line 52, delete "claim 11" and insert -- claim 10 --.

Signed and Sealed this

Twenty-seventh Day of December, 2005

JON W. DUDAS
*Director of the United States Patent and Trademark Office*